US011645609B2

(12) United States Patent
Wang et al.

(10) Patent No.: US 11,645,609 B2
(45) Date of Patent: May 9, 2023

(54) TRACKING FOOD SAFETY IN A SUPPLY CHAIN

(71) Applicant: International Business Machines Corporation, Armonk, NY (US)

(72) Inventors: Xinlin Wang, Irvine, CA (US); Vincent Tkac, Delaware, OH (US)

(73) Assignee: International Business Machines Corporation, Armonk, NY (US)

(\*) Notice: Subject to any disclaimer, the term of this patent is extended or adjusted under 35 U.S.C. 154(b) by 205 days.

(21) Appl. No.: 16/741,732

(22) Filed: Jan. 13, 2020

(65) Prior Publication Data

US 2021/0216960 A1 Jul. 15, 2021

(51) Int. Cl.
*G06Q 10/08* (2023.01)
*G06Q 10/0833* (2023.01)
*G01N 33/02* (2006.01)
*G06Q 50/28* (2012.01)
*G06Q 10/087* (2023.01)
(Continued)

(52) U.S. Cl.
CPC ......... *G06Q 10/0833* (2013.01); *G01N 33/02* (2013.01); *G06Q 10/087* (2013.01); *G06Q 30/018* (2013.01); *G06Q 50/12* (2013.01); *G06Q 50/28* (2013.01)

(58) Field of Classification Search
CPC ............. G06Q 10/0833; G06Q 10/087; G06Q 30/018; G06Q 50/12; G06Q 50/28; G01N 33/02
See application file for complete search history.

(56) References Cited

U.S. PATENT DOCUMENTS 9,849,364 B2 12/2017 Tran et al.
2006/0161392 A1\* 7/2006 Sholl ...................... G06Q 10/08
702/183

(Continued)

FOREIGN PATENT DOCUMENTS

WO 2013071499 A1 5/2013

OTHER PUBLICATIONS

Derby, Mary Patricia, Poison Control Center Foodborne Illness Surveillance, The University of Arizona, 2008.\*

(Continued)

*Primary Examiner* — Nathan Erb
(74) *Attorney, Agent, or Firm* — Jeffrey S LaBaw; Anthony V England; Randy Tejeda

(57) ABSTRACT

Embodiments generally relate to tracking food safety in a supply chain. In some embodiments, a method includes receiving a case identifier associated with a case of food, retrieving food information concerning the food items, analyzing the food information to determine an in-use portion of a distribution path, and associating the case identifier with user identifiers associated with candidate users determined to have purchased one or more of the food items. The method further includes receiving an incident notification message including an indication of a problem with the food item associated with the case, and identifying the case identifier associated the food item associated with the food item identifier in the incident notification message, and retrieving the one or more user identifiers associated with the case identifier, and sending one or more problem notification messages to one or more client devices of one or more candidate users.

20 Claims, 5 Drawing Sheets

(51) Int. Cl.
    *G06Q 50/12*        (2012.01)
    *G06Q 30/018*       (2023.01)

(56) References Cited

U.S. PATENT DOCUMENTS

2011/0022463 A1*  1/2011  Harris .............. G06Q 20/3221
                                                    705/14.51
2011/0098026 A1*  4/2011  Uland .............. G06Q 10/0833
                                                    455/414.2
2016/0034907 A1   2/2016  Worrall et al.
2018/0165771 A1*  6/2018  Lesik ................. G06Q 10/087
2018/0284093 A1   10/2018 Brown et al.

OTHER PUBLICATIONS

IBM, "IBM Food Trust", IBM Blockchain, htttps://www.ibm.com/blockchain/solutions/food-trust [retrieved Jan. 7, 2020].

* cited by examiner

TRACKING FOOD SAFETY IN A SUPPLY CHAIN

BACKGROUND

The supply chain of food has come under more detailed scrutiny by the US Food and Drug Administration (FDA) and other regulatory bodies due to improved access to healthcare data and analytics. Food safety tracking typically ends after food is processed, such as in restaurants, food courts, cafeterias, etc. With weak tracking and slow tracing, a typical food recall can dramatically increase in scope, which in turn increases the cost of a food recall.

SUMMARY

Disclosed herein is a method for tracking food safety in a supply chain, and a system and a computer program product as specified in the independent claims. Embodiments are given in the dependent claims. Embodiments can be freely combined with each other if they are not mutually exclusive.

In an embodiment, a method includes receiving a case identifier from a code sensing system, where the case identifier is associated with a case of food, the case of food including a plurality of food items associated with a plurality of food item identifiers; retrieving food information associated with the case identifier from a database, the food information including information concerning the plurality of food items; analyzing the food information to determine that the plurality of food items are in an in-use portion of a distribution path for the case of food; associating the case identifier with one or more user identifiers in the database, where the one or more user identifiers are associated with one or more candidate users determined to have purchased one or more of the plurality of food items; receiving an incident notification message from a client device, where the incident notification message includes a food item identifier and an indication of a problem with the food item associated with the food item identifier; identifying the case identifier associated with the case of food including the food item associated with the food item identifier in the incident notification message; retrieving, from the database, the one or more user identifiers associated with the case identifier; sending one or more problem notification messages to one or more client devices of one or more candidate users associated with the one or more user identifiers.

In another embodiment, the in-use portion has an in-use start time and an in-use end time, where the in-use start time is based on one or more start time policies. In another aspect, the one or more user identifiers are associated with one or more candidate users determined to have purchased one or more of the plurality of food items in a restaurant. In another aspect, the one or more user identifiers are associated with one or more candidate users determined to have purchased one or more of the plurality of food items in a grocery store. In another aspect, the in-use portion has an in-use start time and an in-use end time, and where the in-use end time is based on one or more end time policies. In another aspect, the method further includes determining user attributes based on one or more user-attribute policies. In another aspect, the method further includes determining food attributes based on one or more food-attribute policies.

DETAILED DESCRIPTION

Embodiments described herein facilitate the tracking food safety in a supply chain. Embodiments ensure increased food safety by tracking food safety in a distribution path of the supply chain until consumed by consumers. Embodiments extend food safety tracking by providing a mapping between food items that are in use (e.g., in process for purchase, consumption, etc.) and candidate customers who may consume that food. In this way, embodiments quickly identify any food issues through a bigger populated consumer data set. For example, embodiments may extend food safety tracking from a restaurant's kitchen to customers' plates.

As described in more detail herein, a system determines an in-use portion of a distribution path for a case of food. In various embodiments, the in-use portion for a given food item starts when a case containing the food item is opened, and the food item is removed from the case. Once the food item is removed from the case, the food item is difficult to track, especially when the food item has no code for tracking. In various embodiments, the in-use portion for a given food item ends when consumed by a consumer. In various embodiments, the system associates the case of food with one or more candidate users. Such users may be, for example, patrons of a restaurant that serves food items from the case of food. In another example scenario, users may be customers at a grocery store that sells food items from the case of food. If the system receives an incident notification, indicating a problem with a food item, the system matches the food item with the problem to the case of food. The system may then send out one or more problem notifications to the one or more candidate users to warn them of potential problems with food items they purchased.

Figure 1:
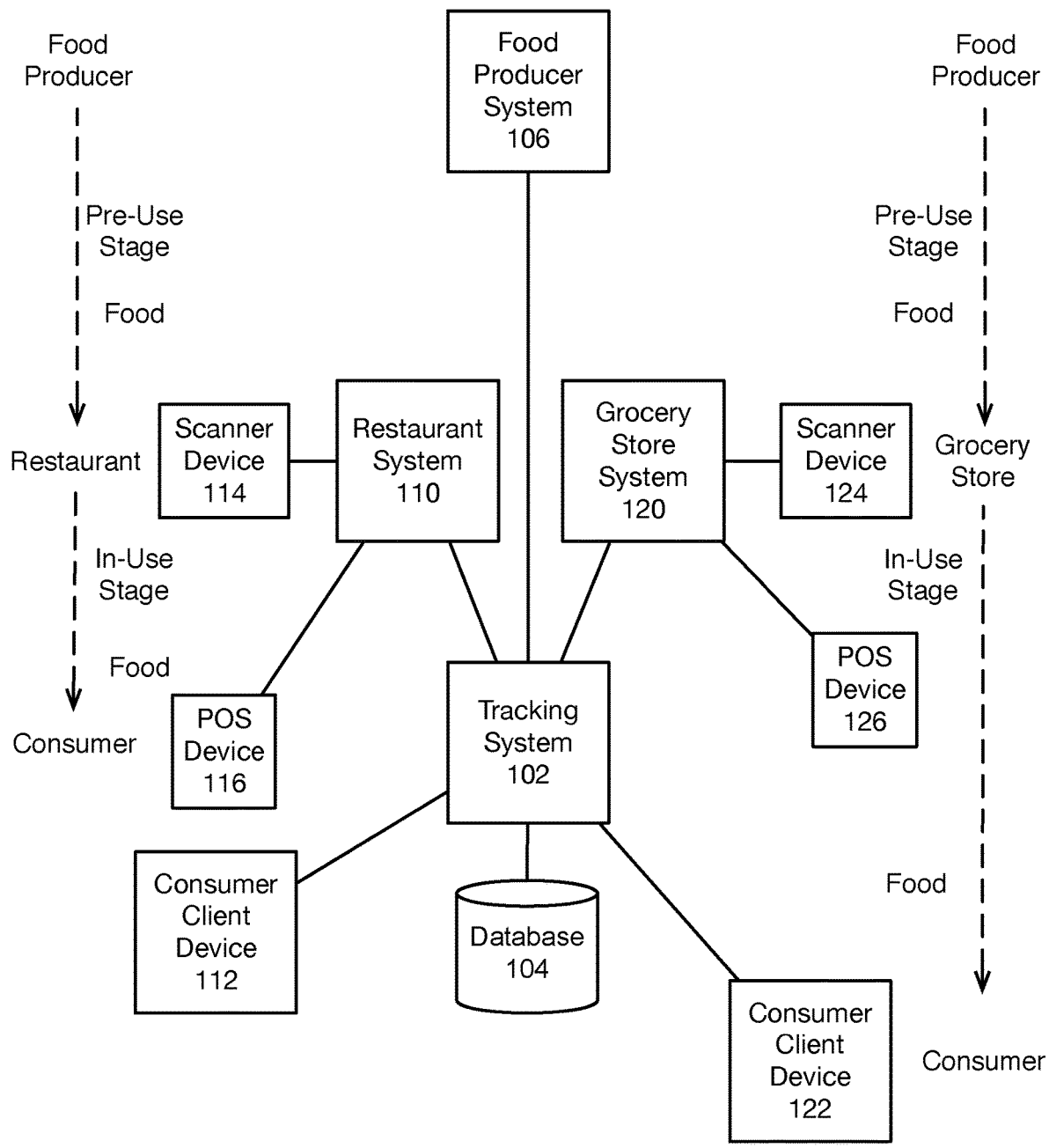
FIG. 1 is a high-level block diagram of an example food distribution environment associated with a food supply chain, which may be used for some implementations described herein.

FIG. 1 is a high-level block diagram of an example food distribution environment 100 associated with a food supply chain, which may be used for some implementations described herein. In some implementations, food distribution environment 100 includes a tracking system 102, a database 104, a food producer system 106, a restaurant system 110, a consumer client device 112, a scanner device 114, a point of service (POS) device 116, a grocery store system 120, a consumer client device 122, a scanner device 124, and a POS device 126.

A food supply chain is generally a broad range of food production-distribution-consumption configurations, which may include food producers, restaurants, grocery stores, markets, etc. A food supply chain may involve various components including purchase, acquisition, logistics, distribution, warehouse, inventory control, etc.

A distribution channel, also referred to herein as a distribution path, is an aspect of supply chain management that involves the movement of products from the food producer to the end user or customer. As shown on the left side of FIG. 1, there is one distribution path from a food producer to a restaurant and then to a consumer. The portion of the distribution path between the food producer and the restaurant may be referred to as the pre-use stage or portion of the distribution path. In various embodiments, the pre-use stage starts at the source of the food (e.g., food producer) and ends at the restaurant. As described in more detail herein, the pre-use stage for a given food item typically ends when the case containing the food item is opened (e.g., at the restaurant).

In various scenarios, when a given case of food arrives at the restaurant, a user may use scanner device 114 to scan a case identifier on the case of food. When a consumer purchases a meal, which may have been prepared with food items from the case of food, POS device 116 is used to perform the purchase transaction. Food information associated with the case identifier, purchase information associated with the food items purchased, and customer information may be stored at restaurant system 110 and/or at database 104 for tracking system 102 to access. In various embodiments, the tracking system records time stamps and geographic locations at various points of the in-use portion of the distribution path. For example the tracking system may record the time stamp and geographic location at the initial sensing of the case identifier, at the point of sale, etc. In various embodiments, the tracking system may store the time stamp and geographic location information in a database (e.g., database 104).

As described in more detail herein, tracking system 102 communicates with food producer system 106, restaurant system 110, grocery store system 120, and consumer client devices 116 and 122. In various embodiments described herein, tracking system 102 communicates with these various entities in order to track food items to determine and/or prevent potential problems that may occur with the food items (e.g., food spoilage, food contamination, etc.). In various embodiments, restaurant system 110 communicates with scanner device 114 and POS device 116, and grocery store system 120 communicates with scanner device 124 and POS device 126. As described in more detail herein, restaurant system 110 and grocery store system 120 collect various information associated with food items and cases in which the food items is shipped. Restaurant system 110 and grocery store system 120 then share this information with tracking system 102 to track food items during the in use portion of the distribution, which is described in more detail below.

The portion of the distribution path between the restaurant and the consumers may be referred to as the in-use stage or portion of the distribution path. In various embodiments, the in-use stage for a given food item starts at the restaurant (e.g., when the case containing the food item is opened) and ends when the food item is consumed by a consumer. The in-use stage may also be referred to as the "last mile" of the distribution path. As shown, embodiments extend the pre-use tracking of a given food item to in-use tracking of the food item by linking the pre-use stage to the in-use stage in terms of tracking food items.

Shown on the right side of FIG. 1 is another distribution path from a food producer, to a grocery store, and then a consumer. The portion of the distribution path between the food producer and the grocery store may be referred to as the pre-use stage or portion of the distribution path. In various embodiments, the pre-use stage starts at the source of the food (e.g., the food producer), and ends at the grocery store. As described in more detail herein, the pre-use stage for a given food item ends when the case containing the food item is opened (e.g., at the grocery store).

In some embodiments, food items with barcodes and with longer shelf lives may extend this pre-use period until the item is scanned at POS device 126 at time of purchase by the end consumer. In another embodiment, online food item orders with longer shelf lives and barcodes may extend the pre-use period until the food item is shipped to the end consumer or received by the end consumer as confirmed by customer delivery package tracking or estimated delivery date.

The portion of the distribution path between the restaurant and the consumer may be referred to as the in-use stage or portion of the distribution path. In various embodiments, the in-use stage for a given food item starts at the restaurant (e.g., when the case containing the food item is opened) and ends when the food item is consumed by a consumer. The pre-use stage of any given distribution path is where food items are conventionally tracked. Unlike conventional solutions, the system tracks food items during the in-use stage.

In various scenarios, when a given case of food arrives at the grocery store, a user may use scanner device 124 to scan a case identifier on the case of food. When a consumer purchases one or more food items, which had been removed from the case of food and put on display for purchase, POS device 126 is used to perform the purchase transaction. Food information associated with the case identifier, purchase information associated with the food items purchased, and customer information may be stored at grocery store system 120 and/or at database 104 for tracking system 102 to access. As indicated above, the tracking system records time stamps and geographic locations at these various points of the in-use portion of the distribution path, and may store the time stamp and location information in a database (e.g., database 104).

While example embodiments are described herein in the context of restaurants and grocery stores, these embodiments and other also apply to other contexts as well. For example, the tracking system may track food items in distribution paths involving food courts, dining halls, school or company cafeterias, etc. to where a given user consumes a given food item being tracked. Embodiments may apply to other non-food items with fixed expiration dates that are sold in retail settings, as well.

For ease of illustration, FIG. 1 shows one block for each of tracking system 102, database 104, food producer system 106, restaurant system 110, consumer client device 112, scanner device 114, point of service (POS) device 116, grocery store system 120, consumer client device 122, scanner device 124, and POS device 126. Blocks 102 to 126 may represent multiple blocks of each block type. In other implementations, environment 100 may not have all of the components shown and/or may have other elements including other types of elements instead of, or in addition to, those shown herein.

While tracking system 102 performs embodiments described herein, in other embodiments, any suitable component or combination of components associated with tracking system 102 or any suitable processor or processors associated with tracking system 102 may facilitate performing the embodiments described herein.

Figure 2:
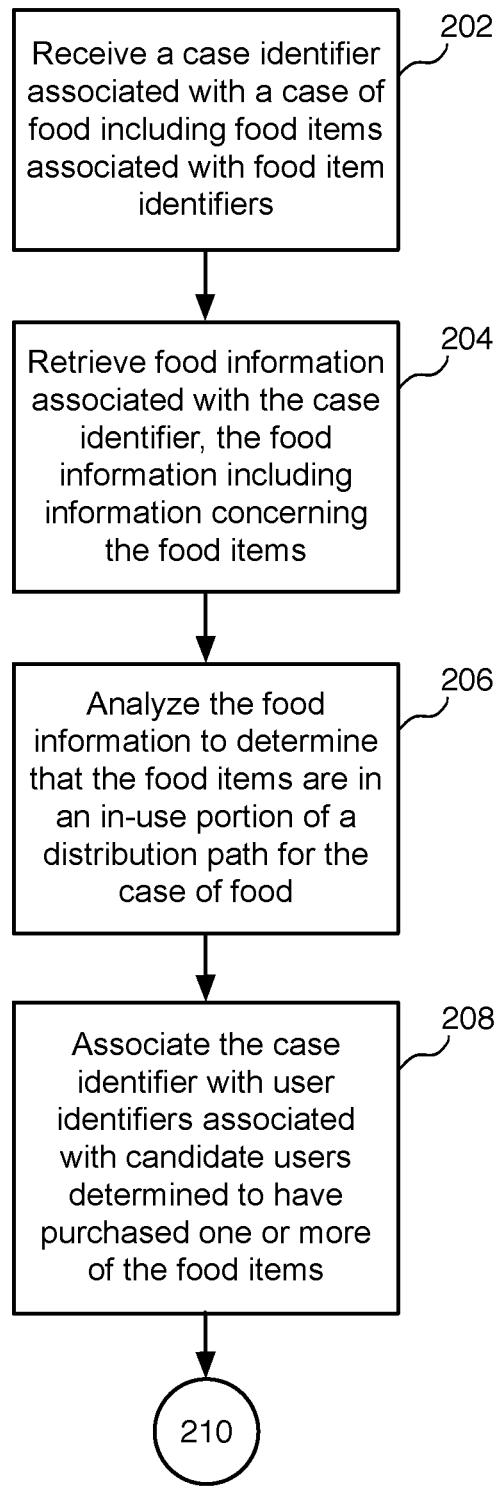
FIG. 2 is an example flow diagram for tracking food safety in a supply chain, according to some embodiments.

FIG. 2 is an example flow diagram for tracking food safety in a supply chain, according to some embodiments. As described in more detail herein, the tracking system determines a time window or in-use stage or portion of a distribution path of a food item. During the in-use stage, the tracking system tracks food safety from a store or restaurant kitchen to a consumer's plate.

Referring to both FIGS. 1 and 2, a method begins at block 202, where a system such as tracking system 102 receives a case identifier from a code sensing system (e.g., scanner device 114, scanner device 124). While some example implementations are described in the context of a sensing system involving a scanner device, these implementations may apply to any suitable sensing system that senses or detects the case identifier. Various example embodiments are described in more detail below. In various embodiments, the case identifier is associated with a case of food, which includes food items associated with food item identifiers.

At block 204, the tracking system retrieves food information associated with the case identifier from a database such as database 104. The food information includes information concerning the food items. In various embodiments, tracking system shares such food information with restaurant system 110 and grocery store system 120.

At block 206, the tracking system analyzes the food information to determine that the food items are in an in-use portion of a distribution path for the case of food. In various embodiments, the beginning in-use portion marks the end of the pre-use portion of the distribution path. The in-use portion of the distribution path is the stage when the food items in the case are put into use. The food items are removed from the case and used for preparing meals in a restaurant, purchased by consumers at a grocery store, etc. As indicated above, the tracking system records time stamp and geographic location during the initial sensing of the case identifier, as well as at points of the in-use portion of the distribution path. The tracking system may store the time stamp and geographic location information in a database (e.g., database 104).

In various embodiments, the in-use portion is based on the opening of the case of food. Once the food items are removed from the case, a physical case identifier attached to the case no longer follows or tracks the individual food item. The case is typically broken down or may be reused for future transportation. Any food information associated with the food items remains accessible to the tracking system's database 104. As such, in various embodiments, the tracking system may deem the case to be in-use upon the opening of the case when the food items are removed.

When the case arrives at its final destination (e.g., restaurant, grocery store, etc.), a physical tag with a case identifier is sensed by the tracking system using any suitable sensing system. The case identifier may be a bar code or symbol. In some embodiments, the case identifier may be sensed by the tracking system using any suitable sensing technology, such as systems involving a scanner device (e.g., scanner device 114, scanner device 124, etc.), radio-frequency identification (RFID) technology, etc. Alternatively, the tracking system may receive the case identifier as a manual input. Manual input may provide some additional accuracy with a possible exact time of opening of the case. However, the system scanning or sensing the arrival of the case provides a reasonable estimate of the time of opening. With a scenario of perishables, cases are predictably opened within a certain time frame of final delivery. The time frame may depend on the particular type of food item (e.g., lettuce versus potatoes, etc.).

In various embodiments, the case of food is associated with a case identifier. The case identifier may be any code that uniquely identifies the case of food. For example, the case identifier may be a bar code, an alphanumeric code, etc. In various embodiments, the case identifier is also associated with food information about the food items in the case. The tracking system may store such food information, including time stamp information, geographic locations, etc. in a database accessible by the system such as database 104. Such information may include, for example, the category of food (e.g., produce, meat, etc.), the specific types of food (e.g., butterhead lettuce, romaine, broccoli, etc.), the quantity (e.g., 24 heads of butterhead lettuce, etc.), food source (e.g., Producer A), pervious locations (e.g., Distributor A), final destination of the case (e.g., Restaurant A, Grocery Story A), etc. The particular types of food information may vary, depending on the particular implementation.

In various embodiments, the in-use portion of the distribution path has an in-use start time and in-use end time. In various embodiments, the in-use start time is based on one or more start time policies. For example, in various embodiments, a start time policy may be that the in-use start time is when the case of food is opened. In various embodiments, the in-use start time includes a day and time of day that a case of a food item is opened. In various embodiments, the tracking system also determines the time stamp and geographic location of the case of food when opened. In various embodiments, the geographic location is the GPS location of the food consumers who purchase the food items, the restaurant staff who process food, or the grocery store staff who handle the food before purchase. For example, the case of food may have been opened in a kitchen of a restaurant, at a grocery store, etc. In some embodiments, the tracking system may receive a case identifier that identifies the case of food. The case identifier may be a data entry or scan of a bar code, etc. upon the opening of the case of food. The tracking system may receive a day and time that the case of food is opened.

In various embodiments, the tracking system determines location information associated with the case of food that is opened. The system may determine the location information using any suitable location technologies such as Global Positioning System (GPS) technology. In some embodiments, the system may access food information associated with the case identifier. The food information may include the final destination and previous location. The food information may also be included in a purchase order that states the final destination. Once scanned, the system may determine if the stated final destination matches the actual current location.

In some embodiments, the location information may include a geographic location. In some embodiments, the location information may include a type of location. For example, in various embodiments, the case of food is opened in a restaurant. In various embodiments, the case of food is opened in a grocery store. Example embodiments directed to restaurant and grocery store use cases are described in more detail herein.

In various embodiments, the tracking system also determines the specific type of food item (e.g., produce, meat, etc.), as well as the location of the food item when taken from its case. As indicated above, the food information associated with the case identifier may include various food attributes, including the type of food item and other relevant information such as shelf life, expiration dates, etc. Various example embodiments involving food attributes are described in more detail herein. Based on such information, the tracking system may estimate a consumption time of the food items in a case. For example, if the food item was prepared in the restaurant, for example, it can be expected that the food item will be in-use until the dish containing the food item is served to a customer. The tracking system may categorize a given food item has a perishable, which would have a shorter shelf life.

In various embodiments, where the in-use portion has an in-use start time and in-use end time, where the in-use end time is based on one or more end time policies. For example, in various embodiments, an end time policy may be that the in-use end time is when the food item has been consumed by a consumer. In some embodiments, an end time policy may be that the in-use end time is when the food item has been reported to the tracking system as having a problem (e.g., spoiled, contaminated, etc.).

At block 208, the tracking system associates the case identifier with one or more user identifiers in the database (e.g., database 104). In various embodiments, the one or more user identifiers are associated with one or more candidate users determined to have purchased one or more of the food items. In some embodiments, the system may determine the candidate users based on their location and time of purchase. In some embodiments, the system may determine candidate users based on customer purchase receipt information, which the system may access at time of an incident report, food product refund, etc. The customer purchase receipt information may include information such as food item identifiers that identify items purchased, the location of purchase, the time of purchase, user identifier, etc. In some embodiments, the one or more user identifiers are associated with one or more candidate users determined to have purchased one or more of the plurality of food items in a restaurant. In some embodiments, the one or more user identifiers are associated with one or more candidate users determined to have purchased one or more of the plurality of food items in a grocery store.

In some embodiments, a user may opt into the tracking system and share some of their information. For example, the tracking system may receive from the user mobile device the user's identity and location when they are on the premises eating in a restaurant, shopping for food, etc. An application on a user's mobile device may send to the tracking system a timestamp, geographical location, etc. In some embodiments, the tracking system may deem a given user a candidate for consumption of a given food item based on him or her being present at the restaurant, store, etc.

In some embodiments, the tracking system may deem a given user a candidate for consumption of a given food item based on an actual purchase of the food item. The tracking system may also receive information associated with the food purchase. For example, such food purchase information may include a picture of a purchase receipt, optical character recognition (OCR) information from a purchase receipt, data directly from the restaurant or store, etc. Such purchase information may include the food item or food item metadata.

In various embodiments, the tracking system determines user attributes based on one or more user-attribute policies. For example, user-attribute policies may include a type of user. For example, a user may be a customer at a restaurant, a customer at a grocery store, etc. In some scenarios, a user may be an employee at a restaurant, at a grocery store, etc. As described in more detail below, different user attributes may affect the tracking of a given food item. For example, if an employee user at a restaurant or grocery store discovers any problems with food items after being removed from the case. While food items in question might not ever reach a consumer user, the employee may enter an incident notification in the tracking system. As such, the tracking system may send a problem notification message to the food producer, distributers, and/or other relevant entity. One or more problem notification messages may be sent to one or more customer users who might have purchased other food items from the same case of food. This may be the case where some food items are sold before the employ noticed a problem with some of the food items. Example embodiments directed to incident notification messages and problem notification messages are described in more detail herein.

Figure 3:
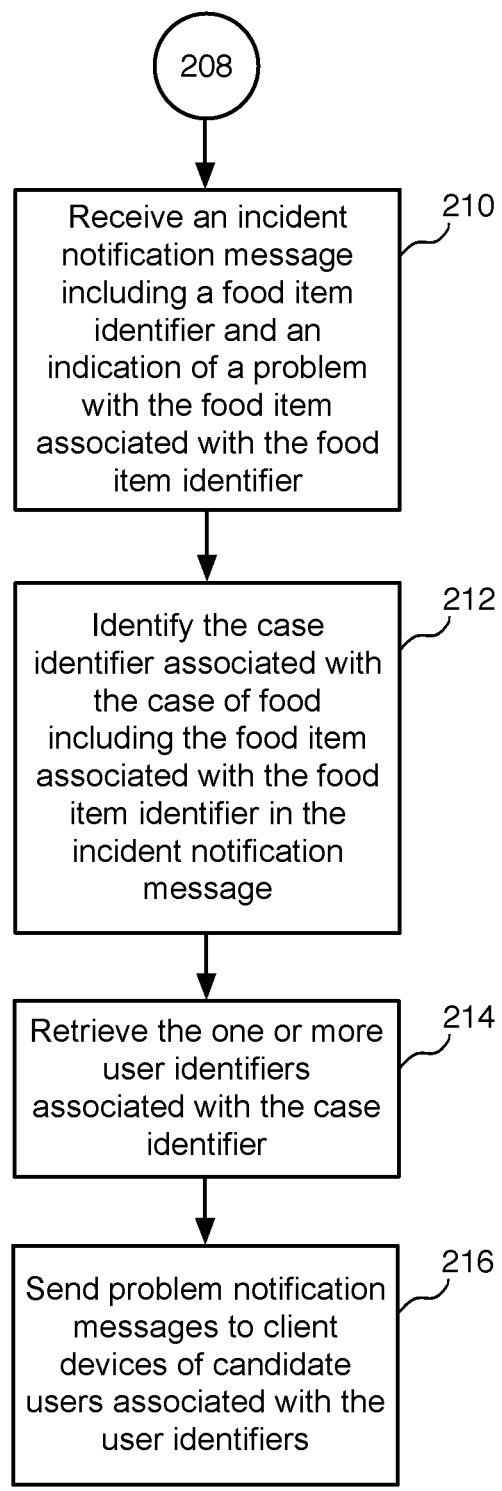
FIG. 3 is an example flow diagram for tracking food safety in a supply chain, continuing from FIG. 2, according to some embodiments.

FIG. 3 is an example flow diagram for tracking food safety in a supply chain, continuing from FIG. 2, according to some embodiments. Referring to FIGS. 1 and 3, at block 210, the tracking system receives an incident notification message from a client device. In various embodiments, the incident notification message includes a food item identifier and an indication of a problem with the food item associated with the food item identifier. In some implementations, the tracking system may enable a user to use a mobile application to report any known food issues or problems that occur during the in-use stage, including the time that the issue was discovered. If no such timing information is received, the tracking system may estimate the time of the incident to be the time of the incident notification.

In various embodiments, the tracking system may determine an in-use end time associated with the case of food, where the in-use end time may be based on one or more end time policies. For example, in some embodiments, an end time policy may that the in-use end time is the time when the incident notification is received. In another example, an end time policy may that the in-use end time is the time entered by a user as to when the incident occurred.

In some embodiments, the tracking system may employ block chain technology in order to provide secure transmission of the incident notification message. Block chain technology may ensure that the incident being reported is not modified by another person.

In various embodiments, the user initiating an incident notification may be a customer. As described in more detail herein, in some scenarios, a given customer may be a customer at a restaurant. In some scenarios, a given customer may be a shopper at a grocery store. In some scenarios, the user may be an employee. For example, in some scenarios, a given employee may be an employee at a grocery store. In some scenarios, the user employee may be an employee at a restaurant. In these examples where the user is an employee, an employee may discover a problem with a particular food item after other food items from the case were purchased by some customers.

At block 212, the tracking system identifies the case identifier associated with the case of food including the food item associated with the food item identifier in the incident notification message. As indicated above, at the start of the in-use stage, the tracking system determines the location and time. The tracking system also determines candidate consumers. As such, if one of those candidate consumers sends an incident notification to the tracking system, the tracking system could determine the case from which the food item was taken. In some embodiments, the tracking system may determine a confidence factor of the match between the reported food item and the case of food that likely contained the food item in question. In some embodiments, the tracking system may determine the inventory at the time of purchase as well as identify the date of arrival of each case, expiration dates associated with the food items in each case, etc. The tracking system may search a database for such food information associated each case. In various embodiments, the tracking system may estimate a time window in which the food items were consumed or sold based on food attributes (e.g., type food, shelf life, etc.). The tracking system may then match the time window to the purchase time of the food item with the problem. During that time window, the tracking system may determine candidate cases from which the food item came. In various embodiments, the tracking system may determine a confidence value for each candidate case, where the confidence value indicates a probability that the food item with the problem came from a particular case.

In various embodiments, the tracking system may link the incident notification with both the pre-use stage and the in-use stage of the distribution path. This facilitates the overall tracking of the food item in the distribution path.

At block 214, the tracking system retrieves, from the database, the one or more user identifiers associated with the case identifier.

At block 216, the tracking system sends one or more problem notification messages to one or more client devices of one or more candidate users associated with the one or more user identifiers. For example, in some embodiments, a problem notification policy may be to report the food problem to all candidate users. In some embodiments, if not all candidate users are certain, a problem notification policy may be to report the food problem to all candidate users having a confidence factor above a predetermined threshold (e.g., 50%) that candidate user indeed purchased food items from the same case of food that contained the reported food item. In some embodiments, a problem notification policy may be to report the food problem up the supply chain (e.g., to the food producer, etc.). In some embodiments, a problem notification policy may be to report the food problem based on food attributes of the food item having a problem. For example, if the food item is purchased in a grocery store, the tracking system may send a problem notification to all customers who opt in and who may have purchased food items from the case of food in question.

In various embodiments, the tracking system determines food attributes based on one or more food-attribute policies. For example, in some embodiments, a food-attribute policy may be to determine if the food is being served in a restaurant. In some embodiments, a food-attribute policy may be to determine if the food is being sold in a store. In some embodiments, a food-attribute policy may be to determine the type of food (e.g., produce, meat, etc.). As indicated above, such food attributes indicate various information about a given food item, such as expected shelf life, expiration date, expected consumption, etc. For example, a food item sold at a restaurant would be expected to be consumed soon after the case is opened in order to ensure freshness of meals. A food item that sold at a grocery store would have a potentially longer in-use time period, because a customer may cook with the food item on the same day or later in the week.

In various embodiments, a user may receive a problem notification (e.g., food recall-alert, etc.) in various ways from the tracking system. For example, the tracking system may broadcast relevant events to people who may be impacted based on the time window and location information. The tracking system may query events based on an identifier of the food item (e.g., such as bar-code) or certain time window from the tracking system, etc. The tracking system may send out problem notification via a smart contact (e.g., if block chain is used), via a rule-based conditional monitoring engine, etc.

The following are example use cases related to a restaurant scenario and a grocery store scenario. In the restaurant scenario, the case of food is opened and becomes in-use in the restaurant. The tracking system may identify customers in the restaurant as candidate consumers of the food item. The tracking system may receive information about candidate consumers from their mobile devices. Such information may include, for example, billing information, frequent shopper card information, etc. Such information may be made available to the tracking system via a restaurant application. Any such information may be securely transmitted in a block chain. The tracking system may confirm via a restaurant application what the user ate and may determine if what the user ate matches with the food item and thus the case that contained the food item. In various embodiments, the tracking system may enable a user to query a block chain directly or via the restaurant application to look for food quality issues.

When the case is opened in a grocery store, the food item becomes in-use and available for purchase. The tracking system may identify customers in the grocery store as candidate consumers of the food item. The tracking system may receive information about candidate consumers from their mobile devices. Such information may include, for example, billing information, frequent shopper card information, etc. Such information may be made available to the tracking system via a grocery store application. Any such information may be securely transmitted in a block chain. The tracking system may confirm via a grocery store application what the user's household ate and determine if what the user's household ate matches with the food item and thus the case that contained the food item. In various embodiments, the tracking system may enable a user to query a block chain directly or via the grocery store application to look for food quality issues.

In some embodiments, the tracking system may communicate with a smart refrigerator, where the smart fridge recognizes the food item from a grocery store application purchase. The smart refrigerator may register the food item with the tracking system (e.g., in a block chain). In some embodiments, if the tracking system is aware of a food quality issue related to a food item that the user has likely purchased, the tracking system may send the problem notification to the user via the smart refrigerator.

Figure 4:
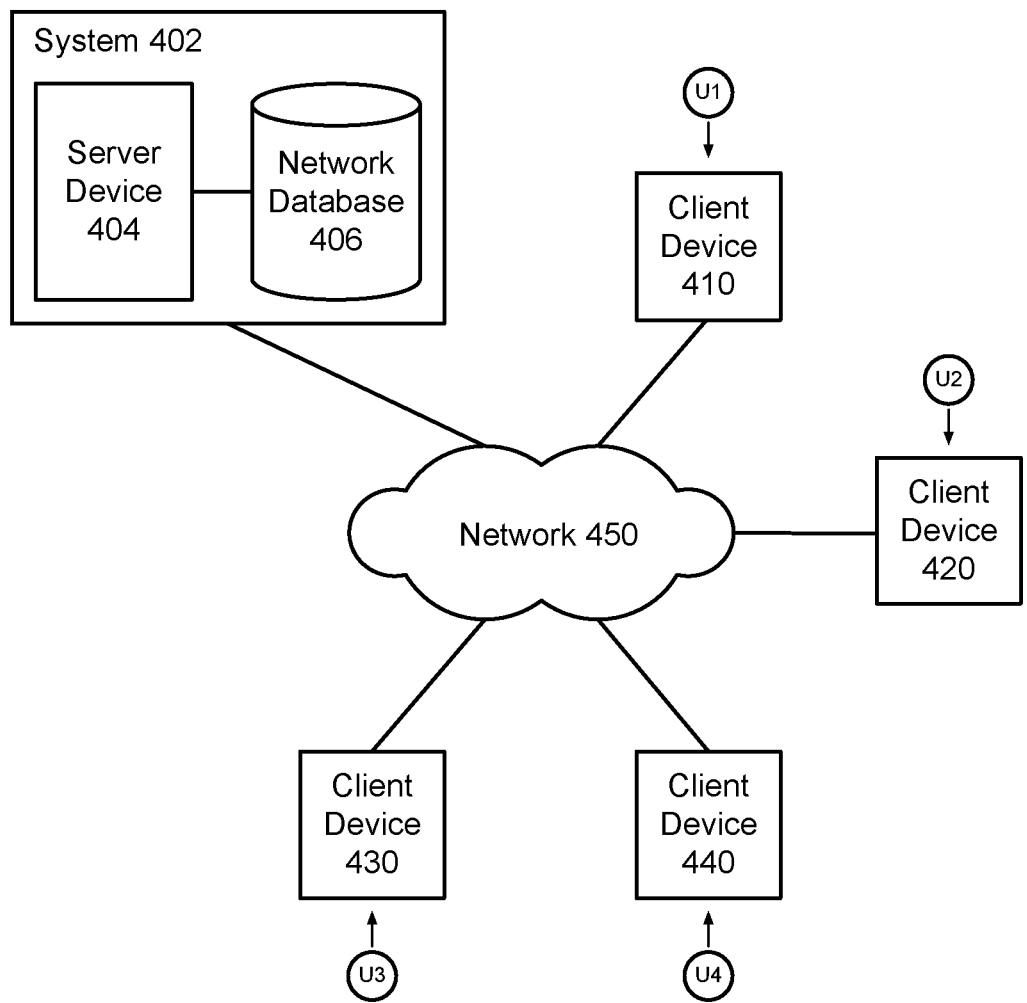
FIG. 4 is a block diagram of an example network environment, which may be used for some implementations described herein.

FIG. 4 is a block diagram of an example network environment 400, which may be used for some implementations described herein. In some implementations, network environment 400 includes a system 402, which includes a server device 404 and a database 406. Network environment 400 also includes client devices 430, 420, 430, and 440, which may communicate with system 402 and/or may communicate with each other directly or via system 402. Network environment 400 also includes a network 450 through which system 402 and client devices 410, 420, 430, and 440 communicate. Network 450 may be any suitable communication network such as a Wi-Fi network, Bluetooth network, the Internet, etc.

For ease of illustration, FIG. 4 shows one block for each of system 402, server device 404, and network database 406, and shows four blocks for client devices 410, 420, 430, and 440. Blocks 402, 404, and 406 may represent multiple systems, server devices, and network databases. Also, there may be any number of client devices. In other implementations, environment 400 may not have all of the components shown and/or may have other elements including other types of elements instead of, or in addition to, those shown herein.

While server 404 of system 402 performs embodiments described herein, in other embodiments, any suitable component or combination of components associated with server 402 or any suitable processor or processors associated with server 402 may facilitate performing the embodiments described herein.

Figure 5:
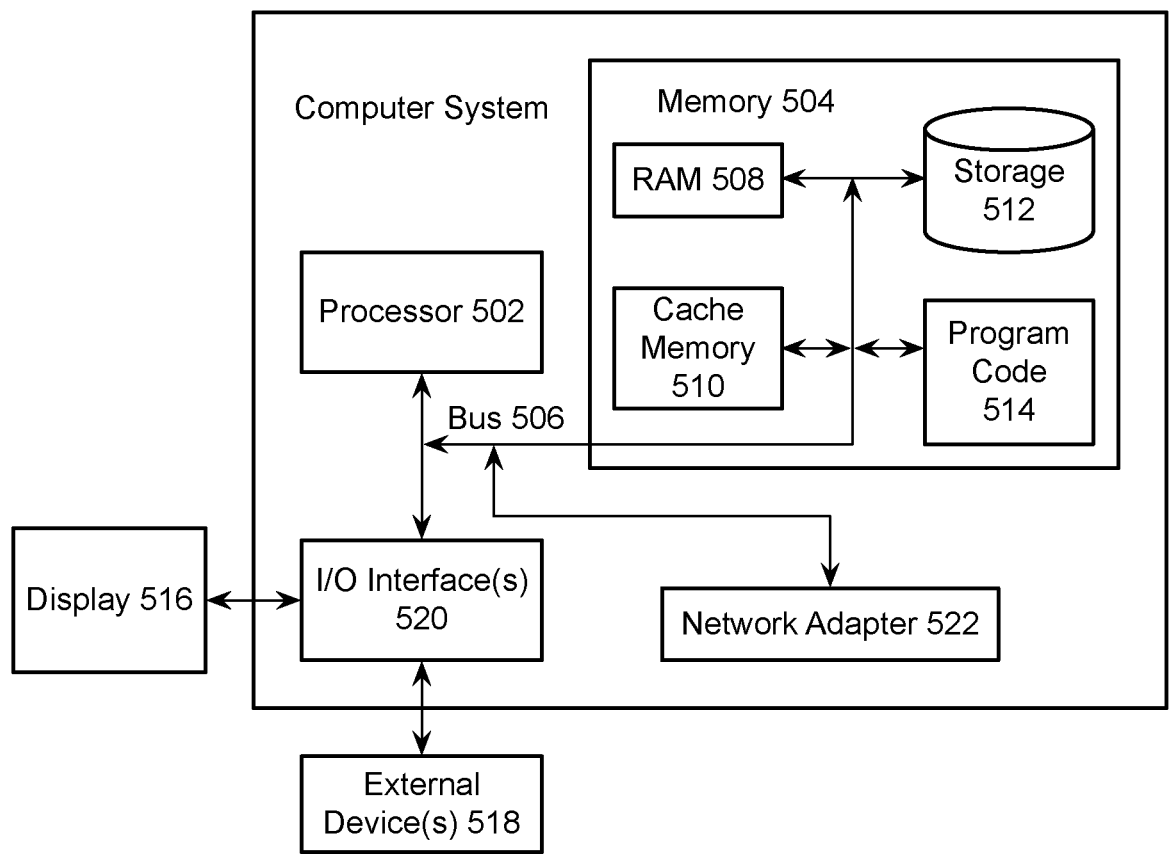
FIG. 5 is a block diagram of an example computer system, which may be used for embodiments described herein.

FIG. 5 is a block diagram of an example computer system 500, which may be used for embodiments described herein. For example, computer system 500 may be used to implement tracking system 102 of FIG. 1, as well as to perform embodiments described herein. Computer system 500 is operationally coupled to one or more processing units such as processor 502, a memory 504, and a bus 506 that couples to various system components, including processor 502 and memory 504. Bus 506 represents one or more of any of several types of bus structures, including a memory bus, a memory controller, a peripheral bus, an accelerated graphics port, a processor or local bus using any of a variety of bus architectures, etc. Memory 504 may include computer readable media in the form of volatile memory, such as a random access memory (RAM) 508, a cache memory 510, and a storage unit 512, which may include non-volatile storage media or other types of memory. Memory 504 may include at least one program product having a set of at least one program code module such as program code 514 that are configured to carry out the functions of embodiments described herein when executed by processor 502. Computer system 500 may also communicate with a display 516 or one or more other external devices 518 via input/output (I/O) interface(s) 520. Computer system 500 may also communicate with one or more networks via network adapter 522. In other implementations, computer system 500 may not have all of the components shown and/or may have other elements including other types of elements instead of, or in addition to, those shown herein.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A tracking system comprising:
   at least one processor and a computer readable storage medium having program instructions embodied therewith, the program instructions executable by the at least one processor to cause the tracking system to perform operations comprising:
   receiving a case identifier over a computer network from a remote computing device for a case of food comprising a plurality of food items each associated with at least one of a plurality of food item identifiers;
   retrieving food information associated with the case identifier from a database resident in the tracking system, the food information comprising information concerning the plurality of food items;
   using the case identifier to determine an in-use start time and a location of an in-use portion of a distribution path for the case of food;
   updating the database by adding one or more user identifiers to the database so that the one or more user identifiers are associated with the case identifier, wherein the one or more user identifiers are associated with one or more candidate users determined to have purchased one or more of the plurality of food items;
   receiving an incident notification message from a client device at a subsequent time from a block chain over the computer network, wherein the incident notification message comprises a food item identifier and an indication of a problem with the food item associated with the food item identifier;
   identifying the case identifier associated with the case of food comprising the food item associated with the food item identifier in the incident notification message;
   retrieving, from the database, the one or more user identifiers associated with the case identifier;
   determining which purchased food items from the case of food are in the in-use portion of the distribution path at the subsequent time and the one or more user identifiers associated with the purchased, in-use food items; and
   sending one or more problem notification messages over the computer network using the block chain to one or more client devices of one or more candidate users associated with the determined one or more user identifiers.

2. The tracking system of claim 1, wherein the in-use start time is based on one or more start time policies.

3. The tracking system of claim 2, wherein the one or more user identifiers are associated with one or more candidate users determined to have purchased one or more of the plurality of food items in a restaurant and the start time policy is a restaurant start time policy, the operations further comprising:
   receiving a timestamp and a geographical location from an application resident on a client device; and
   determining that a user associated with the client device is a candidate user if the timestamp and geographic location indicate that the user was present at the restaurant during the in-use portion of the distribution path at the subsequent time as determined by the restaurant start time policy.

4. The tracking system of claim 2, wherein the one or more user identifiers are associated with one or more candidate users determined to have purchased one or more of the plurality of food items in a grocery store and the start time policy is a grocery start time policy.

5. The tracking system of claim 1, wherein the in-use portion has an in-use end time, and wherein the in-use end time is based on one or more end time policies.

6. The tracking system of claim 1, wherein the tracking system further performs operations comprising determining user attributes based on one or more user-attribute policies.

7. The tracking system of claim 1, wherein the tracking system further performs operations comprising determining food attributes based on one or more food-attribute policies.

8. A computer program product comprising a computer readable storage medium having program instructions embodied therewith, the program instructions executable by at least one processor to cause a tracking system to perform operations comprising:
   receiving a case identifier over a computer network from a remote computing device, wherein the case identifier is for a case of food comprising a plurality of food items each associated with at least one of a plurality of food item identifiers;
   retrieving food information associated with the case identifier from a database resident in the tracking system, the food information comprising information concerning the plurality of food items;
   using the case identifier to determine an in-use start time and a location of an in-use portion of a distribution path for the case of food;
   updating the database by adding one or more user identifiers to the database so that the one or more user identifiers are associated with the case identifier, wherein the one or more user identifiers are associated with one or more candidate users determined to have purchased one or more of the plurality of food items;
receiving an incident notification message from a client device at a subsequent time from a block chain over the computer network, wherein the incident notification message comprises a food item identifier and an indication of a problem with the food item associated with the food item identifier;
identifying the case identifier associated with the case of food comprising the food item associated with the food item identifier in the incident notification message;
retrieving, from the database, the one or more user identifiers associated with the case identifier;
determining which purchased food items from the case of food are in the in-use portion of the distribution path at the subsequent time and the one or more user identifiers associated with the purchased, in-use food items; and
sending one or more problem notification messages over the computer network using the block chain to one or more client devices of one or more candidate users associated with the determined one or more user identifiers;
wherein the tracking system includes at least one processor and a computer readable storage medium having program instructions embodied therewith, the program instructions executable by the at least one processor to perform the operations.

9. The computer program product of claim 8, wherein the in-use start time is based on one or more start time policies.

10. The computer program product of claim 9, wherein the one or more user identifiers are associated with one or more candidate users determined to have purchased one or more of the plurality of food items in a restaurant and the start time policy is a restaurant start time policy.

11. The computer program product of claim 9, wherein the one or more user identifiers are associated with one or more candidate users determined to have purchased one or more of the plurality of food items in a grocery store and the start time policy is a grocery start time policy.

12. The computer program product of claim 8, wherein the in-use portion has an in-use end time, and wherein the in-use end time is based on one or more end time policies.

13. The computer program product of claim 8, wherein the tracking system further performs operations comprising determining user attributes based on one or more user-attribute policies.

14. The computer program product of claim 8, wherein the tracking system further performs operations comprising determining food attributes based on one or more food-attribute policies.

15. A computer-implemented method for tracking food safety by a tracking system, wherein the tracking system includes at least one processor and a computer readable storage medium having program instructions embodied therewith, the program instructions executable by the at least one processor to perform the method comprising:

receiving a case identifier over a computer network from a remote computing device, wherein the case identifier is for a case of food comprising a plurality of food items each associated with at least one of a plurality of food item identifiers;
retrieving food information associated with the case identifier from a database resident in the tracking system, the food information comprising information concerning the plurality of food items;
using the case identifier to determine an in-use start time and a geographic location of an in-use portion of a distribution path for the case of food;
updating the database by adding one or more user identifiers to the database so that the one or more user identifiers are associated with the case identifier, wherein the one or more user identifiers are associated with one or more candidate users determined to have purchased one or more of the plurality of food items;
receiving an incident notification message from a client device at a subsequent time from a block chain over the computer network, wherein the incident notification message comprises a food item identifier and an indication of a problem with the food item associated with the food item identifier;
identifying the case identifier associated with the case of food comprising the food item associated with the food item identifier in the incident notification message;
retrieving, from the database, the one or more user identifiers associated with the case identifier;
determining which purchased food items from the case of food are in the in-use portion of the distribution path at the subsequent time and the one or more user identifiers associated with the purchased, in-use food items; and
sending one or more problem notification messages over the computer network using the block chain to one or more client devices of one or more candidate users associated with the determined one or more user identifiers.

16. The method of claim 15, wherein the in-use start time is based on one or more start time policies.

17. The method of claim 16, wherein the one or more user identifiers are associated with one or more candidate users determined to have purchased one or more of the plurality of food items in a restaurant and the start time policy is a restaurant start time policy.

18. The method of claim 16, wherein the one or more user identifiers are associated with one or more candidate users determined to have purchased one or more of the plurality of food items in a grocery store and the start time policy is a grocery start time policy.

19. The method of claim 15, wherein the in-use portion has an in-use end time, and wherein the in-use end time is based on one or more end time policies.

20. The method of claim 15, further comprising determining user attributes based on one or more user-attribute policies.

* * * * *